(12) United States Patent
Kotov et al.

(10) Patent No.: US 7,534,610 B1
(45) Date of Patent: May 19, 2009

(54) 3D TISSUE CONSTRUCTS ON THE BASIS OF COLLOIDAL CRYSTALS SURFACE MODIFIED BY SEQUENTIAL LAYERING

(75) Inventors: Nicholas A. Kotov, Stillwater, OK (US); Shaopeng Wang, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 616 days.

(21) Appl. No.: 10/460,059

(22) Filed: Jun. 12, 2003

Related U.S. Application Data

(60) Provisional application No. 60/388,376, filed on Jun. 12, 2002.

(51) Int. Cl.
*C12N 5/00* (2006.01)
(52) U.S. Cl. ............ 435/402; 435/325; 435/366; 435/395
(58) Field of Classification Search ............ 435/402, 435/395, 366, 325
See application file for complete search history.

(56) References Cited

U.S. PATENT DOCUMENTS

| | | |
|---|---|---|
| 2002/0037383 A1 | 3/2002 | Spillman, Jr. et al. |
| 2002/0072116 A1 | 6/2002 | Bhatia et al. ............ 435/366 |
| 2004/0038007 A1 | 2/2004 | Kotov et al. |

FOREIGN PATENT DOCUMENTS

WO    WO 00/44507    8/2000

OTHER PUBLICATIONS

Grant et al., "Layer-By-Layer Assembly of Collagen Thin Films: Controlled Thickness and Biocompatibility," *Biomedical Microdevices*, 2001, pp. 301-306, vol. 3, No. 4, Publisher: Kluwer Academic Publishers.
Koktysh et al., "Biomaterials by Design: Layer-By-Layer Assembled Ion-Selective and Biocompatible Films of TiO2 Nanoshells for Neurochemical Monitoring," *Adv. Funct. Mater.*, 2002, pp. 255-265, vol. 12, No. 3, Publisher: Wiley-Vch.
Mendelsohn et al., "Fabrication of Microporous Thin Films from Polyelectrolyte Multilayers," *Langmuir*, 2000, pp. 5017-5023, vol. 16, Publisher: American Chemical Society.
Rogach et al., "Layer-by-Layer Assembled Films of HgTe Nanocrystals with Strong Infrared Emisson," *Chem. Mater.*, Jun. 2, 2000, pp. 1526-1528, vol. 12, Publisher: American Chemical Society.
Rogach et al., "Rasin Bun'- Type Composite Spheres of Silica and Semiconductor Nanocrystals," *Chem. Mater.*, Jun. 27, 2000, pp. 2676-2685, vol. 12, Publisher: American Chemical Society.
Mamedov et al., "Molecular Design of Strong Single-Wall Carbon Nanotube/Polyelectrolyte Multilayer Composites," *Nature Materials*, 2002, pp. 190-194, vol. 1, Publisher: Nature Publishing Group.

*Primary Examiner*—L Blaine Lankford
(74) *Attorney, Agent, or Firm*—Fellers, Snider, Blankenship, Bailey & Tippens

(57) ABSTRACT

A cell growth matrix for optimizing 3D organization nutrient delivery, controlling release of differentiation factors and facilitating attachment of cells to a scaffold Colloidal crystals and inverted colloidal crystals are used to form an ordered structure for use as a scaffold for tissue engineering. The porosity of the cell growth matrix may be modified by the selection of particles of appropriate diameter. Further, the surface of colloidal crystals can be easily modified to accommodate many organic species including biomolecules. Layer-by-layer materials are used for tissue engineering to control cell development by using sequential layering of bioactive species wherein the number and order of LBL layers deposited between layers containing a particular protein are controlled. LBL may also be used for timed release of bioactive species. Increased control differentiation factors release and control of cell attachments to the scaffold are achieved to better mimic natural tissue development.

29 Claims, 9 Drawing Sheets

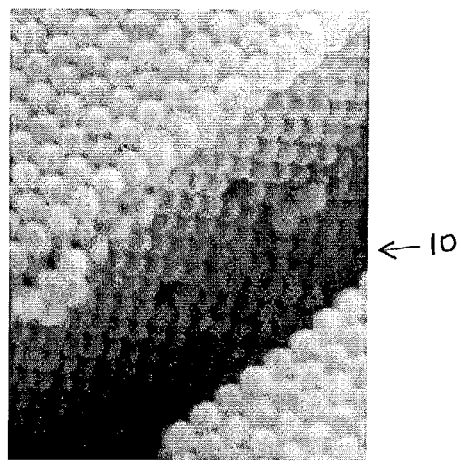
FIG. 1. Layer-by-layer assembly schematics.

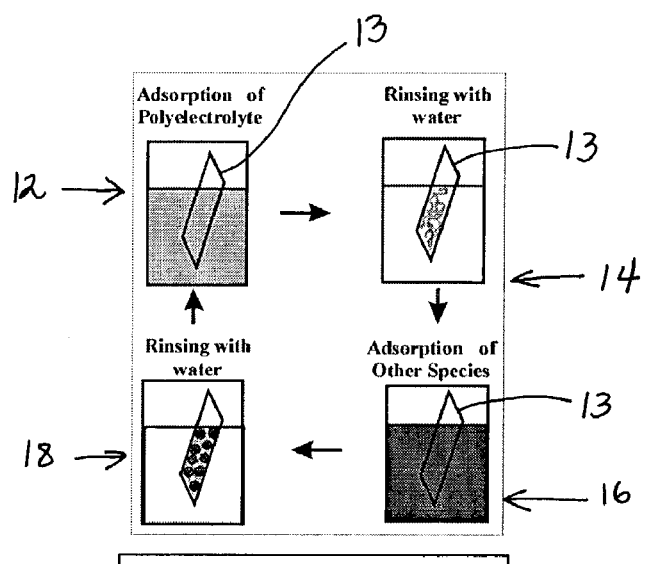
FIG. 2. Model LBL film structure: 1 - polyelectrolyte, 2 - proteins, 3 – particles or different proteins.

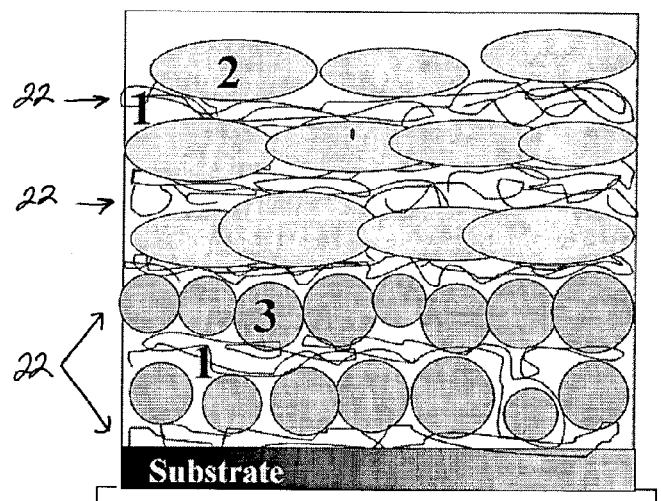
FIG. 3. SEM micrograph of a colloidal crystal made by electrophotetic deposition of latex polymer particles. The diameter of the particles is 600 nm.

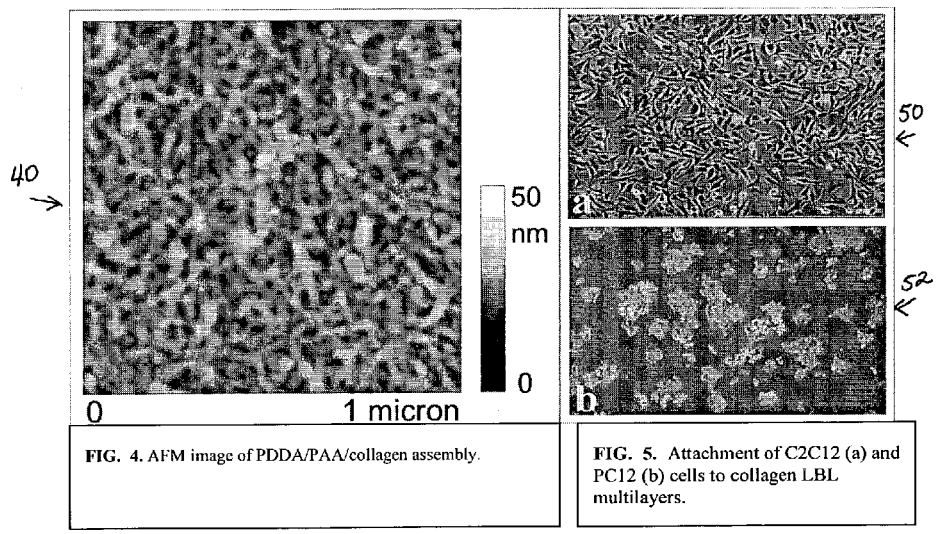
FIG. 4. AFM image of PDDA/PAA/collagen assembly.
FIG. 5. Attachment of C2C12 (a) and PC12 (b) cells to collagen LBL multilayers.

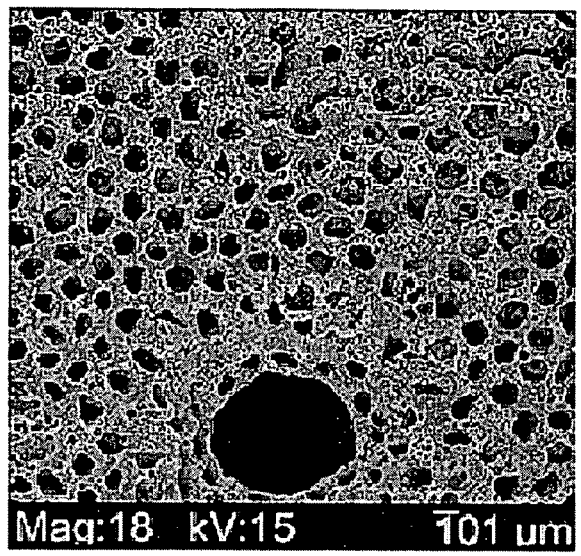
Figure 6A. SEM image of laser-treated scaffold with focused light.

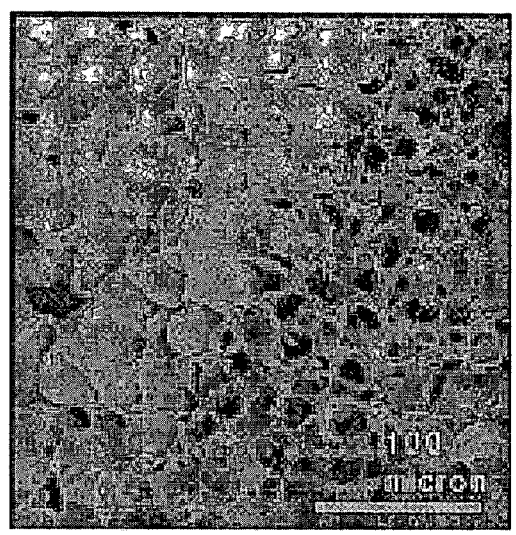
Figure 6B. SEM image of laser-treated scaffold with defocused light. The top left corner represents the untreated surface. The bottom left corner shows opening of the pores after illumination.

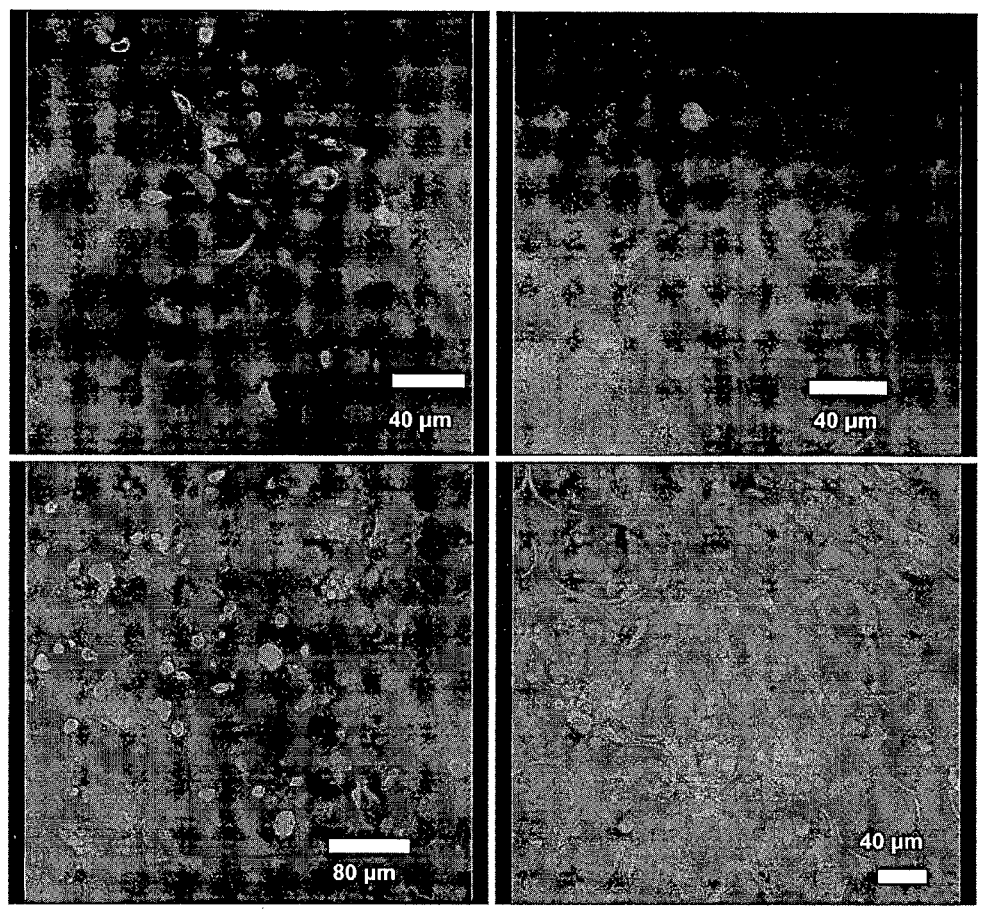
Figure 7A Confocal fluorescence images of stromal cells on the inverse opal scaffold, Top images: bared scaffold; Bottom images: scaffold coated with collagen adhesion layer. From Left to right: day 12 and day 21 after cell seeding, respectively. Cells are stained with 1 μM CFDA SE (carboxyfluorexein diacetate, succinimidyl ester) a few hours prior to imaging.

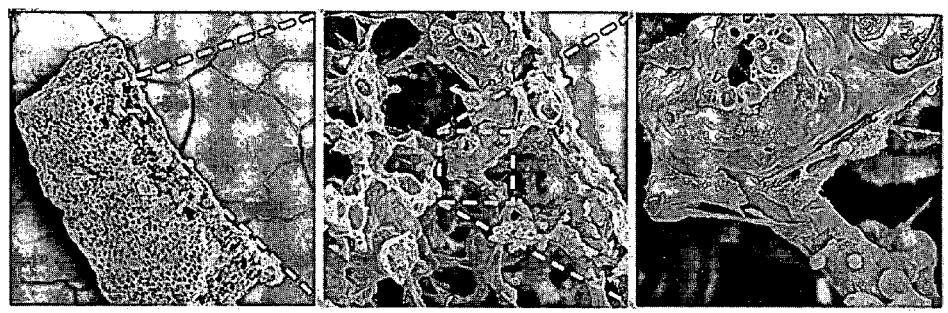
Figure 7B SEM images of human stromal cells (HS-5) cultured on the inverse opal scaffold. The cells were fixed, and the scaffold was freeze-cut to expose the inside. The zoomed images are on the freeze-cut surface section of the scaffold; therefore, represent the distribution of cells inside the scaffold. Size of images (Width × High) from left to right: 3.5×2.9 mm, 300×250 μm, 75×62 μm.

US 7,534,610 B1

3D TISSUE CONSTRUCTS ON THE BASIS OF COLLOIDAL CRYSTALS SURFACE MODIFIED BY SEQUENTIAL LAYERING

CROSS REFERENCE TO RELATED APPLICATION

This application claims the benefit of prior filed copending U.S. Provisional Application Ser. No. 60/388,376, filed Jun. 12, 2002, which application is incorporated herein by reference.

STATEMENT REGARDING FEDERALLY SPONSORED RESEARCH

The Government of the United States of America has certain rights in this invention pursuant to Grant No. BES-0119483 awarded by the National Science Foundation and DARPA Grant No. DAMD17-02-0702.

BACKGROUND OF THE INVENTION

1. Field of the Invention

The present invention relates generally to biological architectural tools, and, more specifically, to the engineering of three-dimensional (3D) tissue constructs on the basis of colloidal crystals (including inverted ones) and layer-by-layer assembly to produce a scaffold for cell growth.

2. Background 3D organization of cells largely determines their function and development. Typical scaffolds for tissue cultures such as lactic acid derivatives, poly(lactide-co-glycolide), fluid microspheres, tantalum-coated carbon matrix, metallic plates, tricalcium phosphonate, hyaluronan sponges, hydroxyapatite, polyester non-woven fabric and others, can provide some degree of spatial organization of the cells. However, their micrometer scale architecture structure is not regular. In order to study the effects of 3D cell contacts one needs a scaffold with distinct order. Well-organized structure of the scaffolds can help to more accurately determine and realize in practice the optimal number and modality of intercell contacts, which is critical for adequate tissue development. Additionally, the uniformity of nutrient fluxes present in ordered systems will be beneficial for achieving homogeneity of cells developing on the scaffolds including stem cell differentiation.

Therefore, it is important to find a method of preparation of cell scaffolds providing 3D crystallinity in the micrometer to millimeter scale as well as space sufficient to accommodate cells, which be achieved in direct and inverted colloidal crystals. Essentially, colloidal crystals are hexagonally ordered lattices of spherical particles with a diameter from several nm to several millimeters. As is well known in the art, the colloidal crystals can be easily self-assembled by sedimentation and then annealed to form solids. Sedimentation of colloidal particles has traditionally been conducted very slowly to organize colloidal crystals into a 3D structure. Other problems known for currently used scaffolds include pH changes during biodegradation which can negatively affect the cell development, biocompatibility with some cell cultures, insufficient cell adhesion and others related to the composition and structure of the scaffold surface. These problems may be substantially alleviated or eliminated by taking advantage of the new surface modification procedure known as layer-by-layer assembly. Due to universality of this technique it can also be applied to achieve desirable surface set of properties and activities for different cell cultures and on different scaffolds. As well, a versatile surface modification procedure can optimization of nutrient delivery and to control the release of differentiation factors and attachment of cells to the scaffold.

"Layer-by-layer" (LBL) is a term used to describe a film deposition process that has been applied for oppositely charged polyelectrolytes. The LBL film deposition process has also been extended to the layer-by-layer assembly of nanoparticle colloids. LBL procedure involves sequentially dipping a substrate into solutions of oppositely charged species alternating with water rinse. In each dipping cycle, a layer of the species, preferably a monolayer or a nanolayer, adsorbs to the substrate. The rinse step removes excess species material. Subsequent dipping cycles result in enhanced adsorption of an oppositely charged species, which is also accompanied by a switch in surface charge. The surface charge switch promotes the adsorption of a following layer. This cycle can be repeated as many times as needed to build up a multilayer of desirable thickness.

One of the major driving forces of LBL is the electrostatic attraction between positive and negative charges located on a solid surface and polyelectrolytes, colloids and other species in solution. Important thermodynamic contributions to film stability are also made by van der Waals interactions. Alternation of layers of positively and negatively charged components is a key principle of the layer-by-layer assembly. The monomolecular nature of layers deposited in each cycle of the LBL technique affords nm scale precision in thin film thickness.

Since the LBL method is quite simple and effective, it has been applied to a variety of charged species from classical inorganic colloids to DNAs. Importantly, assembled biopolymers retain their 3D structure and biological activity. This property of assembled biopolymers has been utilized for enhancement of biocompatibility and attachment of living cells to nanostructured composites.

Overall, there is a recognized need in the field of tissue engineering for well ordered 3D tissue constructs with tunable surface properties. It is thus an object of the present invention to provide methods for engineering improved scaffolds for cell growth.

SUMMARY OF THE INVENTION

According to the present invention, there is provided a cell growth matrix that may be used for mimicking natural tissue development pressures by providing required 3D organization, optimizing nutrient delivery, controlling release of differentiation factors and facilitating attachment of cells to a scaffold. This invention describes a new type of 3D cell growth matrix which can also increase control over its surface properties and other functions such as release of differentiation factors and control of attachment of cells to the scaffold to better mimic natural tissue development.

One aspect of the invention is the use of colloidal crystals and inverted colloidal crystals as a scaffold for tissue engineering. The porosity of the cell growth matrix may be modified by the selection of particles of appropriate diameter. Further, the surface of colloidal crystals can be easily modified to accommodate many organic species including biomolecules.

Another aspect of the invention is the use of layer-by-layer materials for tissue engineering to control cell development by using sequential layering of bioactive species wherein the number and order of LBL layers deposited between layers containing a particular protein are controlled. LBL may also be used for timed release of bioactive species.

A better understanding of the present invention, its several aspects, and its advantages will become apparent to those skilled in the art from the following detailed description, taken in conjunction with the attached drawings, wherein there is shown and described the preferred embodiment of the invention, simply by way of illustration of the best mode contemplated for carrying out the invention.

BRIEF DESCRIPTION OF THE DRAWINGS

FIG. 1 is a SEM micrograph of a colloidal crystal made by electrophotetic deposition.

FIG. 2 is a schematic showing a layer-by-layer assembly.

FIG. 3 is an enlarged view of a model LBL film structure.

FIG. 4 is an AFM image of a PDDA/PAA/collagen assembly.

FIG. 5A is an AFM image of attachment of C2C12 cells to collagen LBL multilayers.

FIG. 5B is an AFM image of attachment of PC12 cells to collagen LBL multilayers.

FIG. 6A is a SEM image of a laser-treated inverse opal scaffold with focused light.

FIG. 6B is a SEM image of a laser treated inverse opal scaffold with defocused light.

FIG. 7A is confocal fluorescence images of stromal cells on the inverse opal scaffold.

FIG. 7B are SEM images of human stromal cell cultured on the inverse opal scaffold.

DETAILED DESCRIPTION OF THE PREFERRED EMBODIMENT

Figure 8:
FIG. 8 is a fluorescence image of stromal cells on a colloidal crystal scaffold (green luminescence).

A new type of cell growth matrix is provided to address problems associated with mimicking natural tissue development. The proposed 3D cell scaffold may be made by the combination of two methods, e.g., layer-by-layer assembly (LBL) and colloidal crystals. While colloidal crystal scaffolds can be used for cell growth even without subsequent surface modification, LBL affords preparation of organized layered systems with programmed properties.

I. Proposed 3D Cell Scaffold.

In the preferred embodiment, the 3D cell scaffold is made by first forming colloidal crystals, as is known in the art, e.g., colloidal crystal 10 (see FIG. 1 which is an SEM micrograph of colloidal crystal made by electrophotetic deposition of latex polymer particles from a suitable material, such as silica or latex). The colloidal crystals are then surface modified by using the LBL approach. The colloidal crystals may also be converted to their inverse replicas producing the so-called inverse colloidal crystals in which the voids are located in place of the spheres. They are typically produced by infiltrating the initially formed crystalline assemblies of the spheres with a curable solution or a sol-gel composition followed by the dissolution or burning of the colloidal spheres. Optionally, laser ablation can be used to further modify the structure of the as formed composition for optimum cell growth and transportation.

Generally, the LBL method involves alternation of layers of positively and negatively charged components. Referring now to FIG. 2, in each dipping cycle, e.g., step 12, a layer, preferably a monolayer or nanolayer, of the species adsorb to substrate 13, while rinse step 14 removes any excess. The next dipping, e.g., step 16, results in enhanced adsorption of an oppositely charged species, which is also accompanied by a switch in surface charge. The switch in surface charge promotes adsorption of the following layer. Preferably, a rinse step, e.g., rinse step 18, follows dipping step 16. This cycle can be repeated as many times as needed to build up a multilayer film with a structure of desired thickness as depicted in FIG. 2. A more detailed description of the layer-by-layer procedure is set out in detail in PCT Publication WO 00/44507, which publication is incorporated herein by reference.

For preparation of the 3D cell scaffold, layers of cell adhesion promoters, differentiation factors, growth factors, and matrix decomposition factors are built up on a solid microporous colloidal crystal by sequentially infiltrating them with appropriate polyelectrolytes, proteins and other species. The microporous support is sequentially immersed into solutions of species A and B with corresponding rinsing steps in between. This sequence of operations constitutes one deposition cycle and results in the production of a film that can be generically denoted (A/B). Repetition of the adsorption and rinsing steps for n times results in the formation of a coating with a generic structure $(A/B)_n$. The repetition of the procedure for a combination of other species, for instance C and D, for m deposition cycles results in the formation of the coating of $(A/B)_n(C/D)_m$ on the microporous scaffold. The species A, B, C, and D species are exemplified by collagen, poly(acrylic acid), cytokines, and polylactic acid respectively. The deposition procedure is expected to work in a wide range of concentrations of the mentioned species in aqueous and other solutions at ambient conditions. The adsorption steps typically last for 0.5-60 min, while the period of rinsing steps normally do not exceed 1 min.

One advantage of this approach is that it results in a highly ordered 3D structure of photonic crystal and its unique optical properties, which can be used to monitor cell attachment and growth. Cell attachment and growth may be monitored by observing the change in scattered, transmitted, or otherwise transformed electromagnetic radiation incident on the photonic crystal during cell development.

Particles of the colloidal crystal solids can be cross-linked together by means of bifunctional chemical agents, polymerizing compounds, ultrasonication, baking, electromagnetic radiation, and other chemical and physical processes. The spheres can also be connected to each other by adsorption of biodegradable polyelectrolytes such as poly(diallyldimethylammonium chloride (PDDA), poly(ethyleneimine) (PEI), poly(allylamine hydrochloride) (PAH), poly(lysine) (PL), poly(acrylic acid) (PAA), poly(lactic acid) (PLA) and/or any others species that can be processed by LBL.

In an alternate embodiment, LBL films can be made from suitable micron-sized particles and weak polyelectrolytes. Both polycations and polyanions are used in the assembly interlacing the strata, which is made of colloidal particles, e.g. 5-10000 nm. Afterwards, the assembly is exposed to fairly acidic or basic solution, which induces formation of pores and channels as described by Mendelson and Rubner, incorporated herein by reference. [Mendelsohn, J. D.; Barrett, C. J.; Chan, V. V.; Pal, A. J.; Mayes, A. M.; Rubner, M. F. Fabrication of Microporous Thin Films from Polyelectrolyte Multilayers. Langmuir (2000), 16(11), 5017-5023.]

The general composition of LBL films includes a bilayer made from weak polycations, such as PAH, PEI, PL, and weak polyanions, such as PAA, PLA. A multilayer from these polyelectrolytes is assembled in strata connecting portions that contain predominantly colloidal particles. After assembly, the film on the substrate is immersed in a fairly low pH solution, e.g., pH 1-4, to induce phase transition in the multilayer made from the weak polyelectrolytes. This process results in formation of pores in the multilayers. The size of the pores depends both on the size of the particles and the assembly conditions. Both of these parameters may be adjusted to obtain microporous substrates suitable for the cell growth. The pore size can be adjusted by changing the diameter of the incorporated particles and by the pH/ionic strength conditions during the assembly and pore formation. Subsequently, the same macroporous system can be sequentially infiltrated with biologically active species similar to the method wherein colloidal crystals are surface modified, as described above for colloidal crystal substrates.

This approach is suitable for preparing cell scaffolds that can be slowly absorbed by the body, if original micron-scale particles are made from biodegradable polymers such as poly (lactic acid).

The particles for colloidal crystals and LBL assembly can be first made from silica by controlled hydrolysis of tetraethylorthosilicate in water/alcohol mixtures. Dispersions of silica or other colloids are allowed to sediment with or without an external electrical field to form a colloidal crystal. The obtained solids may be calcined at 100-1000° C. to achieve a desired structural rigidity. The size and the size distribution of the particles can be controlled with the precision within a few percent by adjusting the nature and concentration of silicating agents, pH, and ionic strength during this procedure.

Inverse opal structures are formed from the colloidal crystal by using a curable solution to infiltrate the pores of the colloidal crystal. After curing the solution (which may be polymetric or may be titania or silica sol-gel), the original colloids are destroyed. If the original colloids are latex (or other polymers) and the inverse opal is made of titania or silica sol-gel, the destruction can be accomplished by heating to burn out the latex (or other polymer), leaving only the inverse opal of titania or silica. Other organic colloids can be leached out from the infiltrated opals by using a correct solvent. If the original colloids are silica, they can be destroyed chemically, for example by hydrofluoric acid.

Preparation of a microporous substrate by the LBL of micron-sized nanoparticles can be made with the same silica or other colloids. The production of a cell growth substrate can be realized by layering not only silica particles but also biodegradable polymer colloidal particles made, for instance, partially or completely from lactic acid copolymers, natural cross-linked proteins, sugars and other compounds and species capable of slow decomposition due to chemical or physical factors. This will allow not only growth of the cells on the substrates, but also allows the substrates to be implanted in place of required organs.

Laser ablation can be used to further modify the scaffold and substrate made using above methods. Vascular like channels can be made by using focused lasers in controllable sizes and distributions on the scaffolds, and lower intensity lasers (unfocused beam) can be used to enlarge the connections between pores in the inverse opal, to optimize the cell seeding/harvest and nutrient transportation.

II. Cell Scaffolding with LBL Films.

Once a skeleton of cell scaffolds is obtained, an LBL film formed of cell growth factors, differentiation factors, and cell adhesion promoters can be accomplished. The LBL film is created by a sequential dipping/rinsing process as discussed above and shown in FIG. 2. The sequence of dipping cycles determines the sequence of deposited layers. The connecting polyelectrolytes act in many ways as molecular glue for the biologically active species that control development of the cells. The connecting polyelectrolytes can be made biodegradable. The stem or other cells that coat the matrix will first come in contact with adhesion promoters, then with growth factors, and then with differentiation agents.

The use of LBL-made materials can be used for control of cell development by using sequential layering of bioactive species. For example, time of "delivery" of a particular protein to cells can be easily controlled by the number of LBL layers deposited between the protein containing layer and the cells. The delivery of the desirable protein can be accomplished either via its slow diffusion or through the top coating or via the decomposition of the latter. The density of the coating and its chemical nature affects when a particular protein will come in contact with the cell. Controlling time of delivery allows programming of cell development by providing the deposited films in a particular order. It is desirable for the entire microporous matrix to be coated conformally and uniformly regardless of the geometry of crevices, channels and voids. A uniform coating will create fairly similar conditions and timing of different stages for virtually all cells attached to the scaffold. Since LBL is a technique based on adsorption, the LBL assembly procedure can create such a uniform, conformal coating.

Following preparation of the cell scaffolds, the cell scaffolds are coated with LBL films from materials such as collagen and cell growth factors. LBL films of collagen are easily made on a variety of materials. The LBL films, e.g., a PDDA/PAA/collagen assembly 40 (FIG. 4) have a highly porous mesh-like structure, which promotes attachment and growth of a variety of cells.

Examples of cells include C2C12, designated generally 50 as shown in FIG. 5A and PC12, designated generally 52 as shown in FIG. 5B. Cells 50 and 52 are shown attached to collagen LBL layers.

III. Use.

In addition to the slow digestion of the LBL films, LBL may also be used for timed release of bioactive species. Examples of bioactive species include but are not limited to: liposomes, capsules, zeolites and others. Timed release of bioactive species can also be accomplished by external signals, such as force field, light, mechanical stress and others.

Culturing of stem and other cells can be done by techniques appropriate to each cell variety, which may need to be optimized for efficient growth in 3D cell scaffolds. The size of the particles incorporated in the described 3D scaffolds can be used to control porosity of the scaffold and therefore control the rate of delivery of nutrients and removal of products of cell metabolism. Since the colloidal particles can be synthesized in a wide variety of diameters from 1 nm to 1 micron and above, the porosity of the scaffold can also be controlled in the same range.

Colloidal crystals can be shaped into desirable objects both prior and subsequent to the biological processing. The actual choice will likely depend on the specifics of organ and tissue requirements. Colloidal crystal tissue constructs can be shaped by allowing sediment in a container of desired geometry. Rigid materials as well as "soft" 3D scaffolds can be made from colloidal crystals cross-linked by chemical means (polyelectrolytes) by machining the calcined solid. Laser ablation of the scaffolds can be used as a type of machining. It may be necessary to incorporate absorptive agents (such as dyes or nanoparticles) into the scaffold to absorb the laser light.

In some instances, organ shaping can be done by simple bending of the substrate. As an example, a cell adhesion promoter may be LBL deposited on a thin fiber from glass, carbon, biodegradable polymer or other material to facilitate the adhesion and differentiation of neural cells. After that, the material having LBL deposited thereon is immersed in a cell culture of neural tissue. The cells adhere along the fiber also extending processes along it. The shaping of the construct to use as a prosthetic device for neural tissue can be as simple as bending the flexible fiber into a desirable shape.

The described 3D cell scaffold may be used for tissue replacement in live organisms. Additionally, they may be used in a bioreactor for production of bioactive species such as vaccines. In this case, the rigid 3D scaffolds based on photonic crystals and microporous LBL materials may be particularly advantageous.

The grown cells can be harvested from the scaffolds. Harvesting of cells may be accomplished by introduction of special layers in the LBL film structure made from polymers, colloids, proteins and other species, that can lose their structural integrity under chemical exposure, action of bioactive species and/or external force fields, light, mechanical stress, etc.

The method and resulting constructs of the present invention have many advantages. Among other advantages, this proposed approach to cell scaffolding provides exceptional advantages for tissue engineering including:

(1) the porosity of the material can be very well controlled to provide optimum nutrient accessibility and support of the cells;
(2) the material can be molded into any desirable shape;
(3) surface modification of the colloidal particles (photonic crystal) or pores (LBL microporous composite) provides optimum adhesion of stem cells;
(4) special biological factors can be incorporated in a structure of the multilayers in a desired order so that the cells receive time-programmed signals. For example, one can incorporate a layer of cytokines underneath the layer of adhesion promoter such as collagen; and
(5) special structural layers can be put in the foundation of the LBL multilayer structure that can disrupt the connectivity of the multilayers by the action of the external fields or other stimuli. Thus, the entire assembly may be delaminated and the attached cells released. For instance, a polyelectrolyte undergoing a photoinduced decomposition can be deposited prior to cell adhesion promoters. Then, the illumination with light will cause the breakdown of the connectivity in the polyelectrolyte multilayers, and therefore, the delamination of the top layers.

The present invention will be further understood with reference to the following non-limiting experimental examples.

EXAMPLE 1

A colloidal crystal is formed. A centrifugation tube was cut and was stuck on a glass plate. The equal volume mixture of the aqueous solution of 75 μm 0.27% polystyrene beads and 1:1 H2O/DMF solution was dropped in the tube. Then the tube was placed in a beaker, which was covered with aluminum foil with small holes and then heated at 60° C. The solution was evaporated slowly and colloidal crystals were obtained after 2-3 days.

EXAMPLE 2

Na2SiO3 solution was diluted with equal volume deionized water and then was infiltrated into the resulting colloidal crystals, which were dried in air naturally to let Na2SiO3 sol become gel. The infiltrating procedure could be repeated two times. After heating at 110° C. for 1 h, the matrix was calcinated in air at 600° C. for 30 min. The 3D scaffolds were obtained.

EXAMPLE 3

The scaffold geometry was modified and vascular structure was introduced into the scaffold for improved cell seeding/harvest and nutrient delivery by laser ablation of the scaffold. Inverse opal scaffolds were subjected to 308 nm excimer laser radiation for 10 pulses over the area of 1.55 cm$^2$. Efficient removal of the matrix was observed. This treatment can be used to modify the scaffolds to improve the nutrient delivery to the cells. FIG. 6A shows an SEM image of a vascular like structure introduced by focused laser beam on the scaffold. The experiment demonstrated the ability to introduce size controllable channels into the scaffold for optimal transportation into the scaffold.

FIG. 6B shows an SEM image of laser-treated scaffold with defocused light. The top left corner represents the untreated surface. The bottom left corner shows opening of the pores after illumination. This experiment demonstrated an optical way to modify the pore and connection channel size.

EXAMPLE 4

The layer-by-layer films were deposited after the inverse opal samples had been cured. The deposition sequence was 10 minutes in a 0.5% polydiallyldimethylammonium chloride (PDDA) aqueous solution (pH set to 3 with HCl/NaOH), rinse with water, 10 minutes in a 0.5% poly(acrylic acid) (PAA) aqueous solution (M.W.=450,000, pH set to 4), rinse, 20 minutes in a 0.1% aqueous solution of collagen III (pH set to 4), rinse, 10 minutes in the PAA solution, rinse, 20 minutes in the collagen III solution, and rinse.

EXAMPLE 5

Growth of Stromal Cells on the Coated Inverse Opal Scaffold

Human stromal cell (HS-5, ATCC Catalog# CRL-11882) was seeded on the inverse opal scaffold, placed in a 24 well cell culture plate and incubated at 37° C. and 5% $CO_2$ level. ATCC recommended culture medium was used: Dulbecco's modified Eagle's Medium with: 4 mM L-glutamine, 4.5 g/L glucose, 1.5 g/L sodium bicarbonate (ATTC 30-2002), supplemented with: 10% fetal bovine serum (ATCC 30-2021), and 1% penicillin-streptomycin (Sigma P3539). Medium were changed every 2~4 days according to the cell growth rate.

The cell adhesion and proliferation was visualized via confocal fluorescence microscopy and scanning electron microscopy (SEM). FIG. 7A shows the confocal images of stromal cell growth on the scaffold with and without LBL coated collagen adhesion layer. Cells are stained with low concentration (1 μM) CFDA SE (carboxyfluorexein diacetate, succinimidyl ester) a few hours prior imaging to reduce disturb of normal cell growth. The excitation wavelength is 488 nm, and emission is collected between 515 and 550 nm. Stromal cells were observed to adhere, proliferate and grow exceptionally well on the prepared 3D scaffolds. The cell growth rate is clearly higher on the collagen coated scaffold.

FIG. 7B shows the SEM image of stromal cells inside the scaffold. The cells were fixed, and the scaffold was freeze-cut to expose the inside. The zoomed images are on the freeze-cut surface section of the scaffold; therefore, they represent the distribution of cells inside the scaffold. The true 3D organization of stromal cells has been obtained. The organization of the cells resembles that of the bone marrow tissue.

FIG. 8 shows a fluorescence image of stromal cells on a colloidal crystal scaffold (green luminescence).

It will be apparent to those skilled in the art that the process herein described for producing a scaffold for cell growth and tissue engineering can be adapted in a multitude of ways.

While the invention has been described with a certain degree of particularity, it is manifest that many changes may be made in the details of the process of assembly without departing from the spirit and scope of this disclosure. It is understood that the invention is not limited to the experimental methods set forth herein for purposes of exemplification.

We claim:

1. A method of facilitating cell growth and tissue engineering with a scaffold comprising:
   immersing a porous colloidal crystal structure into a solution or dispersion comprising PDDA under conditions such that the PDDA coats
   said porous colloidal crystal structure with a thin film comprised of PDDA to form the scaffold, said PDDA having an affinity for said porous colloidial crystal structure;
   seeding cells on said scaffold;
   culturing said scaffold, where said cells are allowed to perform their biological functions.

2. The method according to claim 1 further comprising:
   at least one of rinsing and drying said porous colloidal crystal structure.

3. The method according to claim 1 wherein:
   said step of coating further comprises additional steps of rinsing said porous colloidal crystal structure with a solvent.

4. The method according to claim 1 wherein:
   said step of coating further includes drying the porous colloidal crystal structure after rinsing.

5. The method according to claim 1 further comprising:
   monitoring cell attachment and growth by observing a change in phenomena selected from the group consisting of scattered, transmitted, and otherwise transformed electromagnetic radiation incident on the colloidal crystal.

6. The method according to claim 1 wherein:
   said colloidal crystal is sedimented in a mold to achieve a desired shape.

7. The method according to claim 1 wherein:
   laser ablation is used to obtain a desired shape of the scaffold.

8. The method according to claim 1 wherein:
   mechanical manipulation is used to obtain a desired shape of the scaffold.

9. The method according to claim 1 wherein said biological functions of said cells are selected from a group consisting of adhesion, growth, proliferation, differentiation, migration, apoptosis, self organization into tissue, and combinations thereof.

10. The method according to claim 1 wherein:
    said porous colloidal crystal structure is an inverse opal or inverted colloidal crystal.

11. The method according to claim 10 further comprising:
    monitoring cell attachment and growth by observing the change in phenomena selected from a group consisting of scattered, transmitted, or otherwise transformed electromagnetic radiation incident on said inverse opal.

12. The method according to claim 10 wherein:
    said inverse opal is sedimented in a mold to achieve a desired shape.

13. The method according to claim 10 wherein:
    said inverse opal is machined to achieve the desired shape.

14. The method according to claim 10 wherein:
    laser ablation is used to obtain a desired shape of the scaffold.

15. The method according to claim 10 wherein:
    mechanical manipulation is used to obtain a desired shape of the scaffold.

16. The method according to claim 10 further comprising:
    including layers in the coating that lose their structural integrity when exposed to treatments selected from a group consisting of chemicals, bioactive species, mechanical forces, electric fields, magnetic fields, and electromagnetic radiation.

17. The method according to claim 1 further comprising a step of immersing said porous colloidal crystal structure in a second solution or dispersion of a second substance, said second substance having an affinity for said first substance.

18. The method according to claim 17 wherein:
    said dispersion or solution of second substance is a solution or dispersion comprising bioactive species selected from a group consisting of cell adhesion promoters, differentiation factors, and growth factors.

19. The method according to claim 18 wherein:
    said cell adhesion promoters comprise collagen or extracellular matrix, or combinations thereof.

20. The method according to claim 18 wherein:
    said differentiation factors are selected from a group consisting of cytokines, chemokines, proteins, proteins carried by liposomes, and combinations thereof.

21. The method according to claim 18 wherein:
    said layer containing said bioactive species is further coated with sacrificial layers that decompose at a desired rate for controlling a time at which said bioactive species will be released.

22. The method according to claim 21 wherein:
    said bioactive species is in a top layer of said scaffold.

23. The method according to claim 21 wherein:
    said layer containing said bioactive species is further coated with sacrificial layers that allow a release of said bioactive species when said bioactive species is exposed to external signals selected from a group consisting of mechanical forces, electric fields, magnetic fields, and electromagnetic radiation.

24. The method according to claim 17 further comprising:
    repeating said immersing steps a predetermined number of times.

25. The method according to claim 17 further comprising:
    at least one repetition of said step of immersing said porous colloidal crystal structure in a solution or dispersion of PDDA wherein said solution or dispersion of PDDA is replaced with a solution or dispersion of a third substance, said third substance having an affinity similar to PDDA.

26. The method according to claim 17 wherein:
    at least one repetition of said step of immersing said porous colloidal crystal structure in a solution or dispersion of a second substance wherein said second solution or dispersion is replaced with a solution or dispersion of a third substance, said third substance having an affinity similar to PDDA.

27. The method according to claim 17 wherein:
    said dispersion or solution of at least one of said PDDA and second substance is a solution or dispersion comprising matrix decomposition factors.

28. The method according to claim 1 further comprising:
including layers in the coating that lose their structural integrity when exposed to treatments selected from a group consisting of chemicals, bioactive species, mechanical forces, electric fields, magnetic fields, and electromagnetic radiation.

29. The method according to claim 1 further comprising the steps of:
rinsing said porous colloidal crystal structure with water;
coating said porous colloidal crystal structure in PAA aqueous solution to form a thin film on said porous colloidal crystal structure;
rinsing said porous colloidal crystal structure with water;
coating said porous colloidal crystal structure in an aqueous solution of collagen IIII to form a thin film on said porous colloidal crystal structure;
rinsing said porous colloidal crystal structure with water;
coating said porous colloidal crystal structure in PAA aqueous solution to form a thin film on said porous colloidal crystal structure;
rinsing said porous colloidal crystal structure with water;
coating said porous colloidal crystal structure in an aqueous solution of collagen IIII to form a thin film on said porous colloidal crystal structure;
rinsing said porous colloidal crystal structure with water.

* * * * *